United States Patent [19]

Sluetz et al.

[11] Patent Number: 4,662,382
[45] Date of Patent: May 5, 1987

[54] PACEMAKER LEAD WITH ENHANCED SENSITIVITY

[75] Inventors: James E. Sluetz; Benjamin D. Pless; Paul R. Spehr, all of Freeport, Tex.

[73] Assignee: Intermedics, Inc., Angleton, Tex.

[21] Appl. No.: 692,352

[22] Filed: Jan. 16, 1985

[51] Int. Cl.$^4$ ............................................. A61N 1/04
[52] U.S. Cl. ................................. 128/785; 128/419 P
[58] Field of Search .................... 128/419 P, 784–786

[56] References Cited

U.S. PATENT DOCUMENTS

| | | | |
|---|---|---|---|
| 3,757,789 | 9/1973 | Shanker | 128/404 |
| 4,010,755 | 3/1977 | Preston | 128/404 |
| 4,033,357 | 7/1977 | Helland et al. | 128/418 |
| 4,365,639 | 12/1982 | Goldreyer | 128/786 |
| 4,402,328 | 9/1983 | Doring | 128/786 |
| 4,444,195 | 4/1984 | Gold | 128/642 |
| 4,463,765 | 8/1984 | Gold | 128/419 P |

FOREIGN PATENT DOCUMENTS

| | | |
|---|---|---|
| 0032356 | 12/1980 | European Pat. Off. |
| 0126981 | 4/1984 | European Pat. Off. |
| 2516848 | 4/1975 | Fed. Rep. of Germany |
| 3025955 | 7/1980 | Fed. Rep. of Germany |
| 3046667 | 12/1980 | Fed. Rep. of Germany |
| 3230081 | 8/1982 | Fed. Rep. of Germany |
| 48010 | 10/1980 | World Int. Prop. O. ......... 128/786 |

OTHER PUBLICATIONS

Goldreyer et al., "A New Orthogonal Approach for P-Wave Sensing".
Goldreyer et al., "Orthogonal Ventricular Electrogram Sensing", Pace, vol. 6, Jul.–Aug. 1983, pp. 761–768.
Goldreyer et al., "A New Orthogonal Lead for P Synchronous Pacing", Pace, vol. 4, Nov.–Dec. 1981, pp. 638–644.
Goldreyer et al., "Orthogonal Electrogram Sensing", Pace, vol. 6, Mar.–Apr. 1983, Part II, pp. 464–469.
Hughes, Jr. et al., "Failure of Demand Pacing with Small Surface Area Electrodes", Oct. 1975, pp. 128–132.

Primary Examiner—William E. Kamm
Attorney, Agent, or Firm—Willian Brinks Olds Hofer Gilson & Lione Ltd.

[57] ABSTRACT

A cardiac pacemaker lead has a structure which provides an enhanced sensitivity to atrial P-waves. The distal end of the lead has two sensing electrodes disposed thereon to contact atrial cardiac tissue and to detect near field P-waves with greater sensitivity than far field R-waves.

38 Claims, 13 Drawing Figures

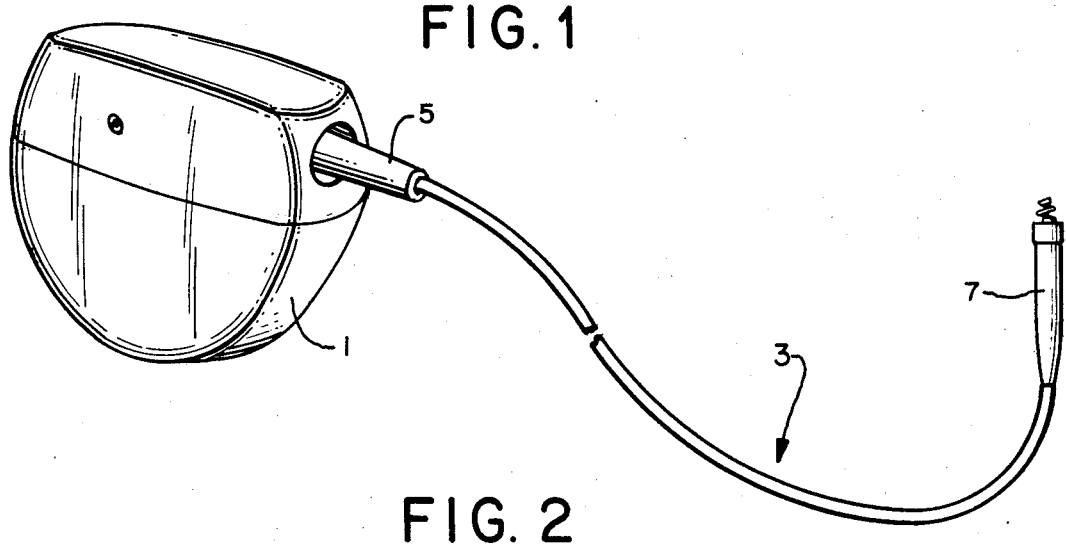
FIG. 1
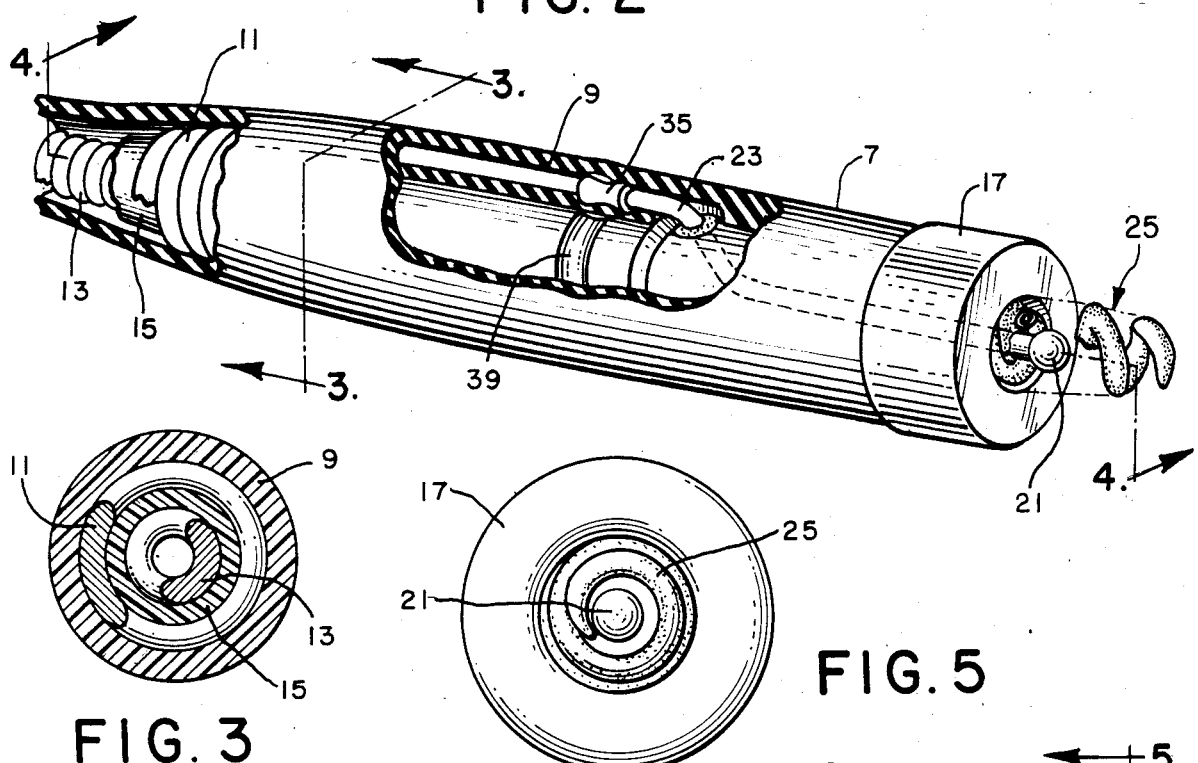
FIG. 2
FIG. 3
FIG. 5
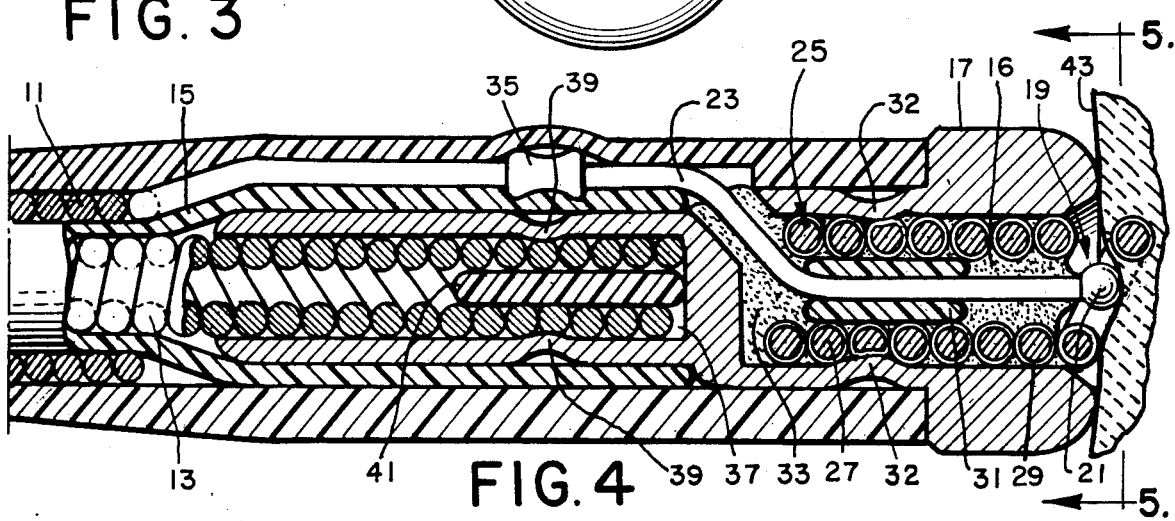
FIG. 4

PACEMAKER LEAD WITH ENHANCED SENSITIVITY

TECHNICAL FIELD

The invention concerns a pacemaker lead with an electrode structure which allows electrical signals of the heart to be detected with greater sensitivity. More particularly, the invention relates to such a lead which provides two relatively closely spaced sensing electrodes at the tip portion of the lead for rejecting far field electrical signals and concentrating sensing at the distal tip of the lead.

BACKGROUND OF THE INVENTION

In a diseased heart the natural electrical system of the heart is disrupted so that the heart cannot sustain a normal pumping rhythm by itself. A pacemaker is therefore required to provide timed electrical stimulation signals to either or both of the atrium and ventricle of the heart. It is well-known that pacemakers may also sense natural electrical activity in the atrium or ventricle and automatically inhibit stimulation or pacing in response to appropriately timed natural electrical activity.

In operation, a pacemaker is typically implanted within the body in the chest cavity of the patient and an electrically conducting pacing lead is positioned within the body between the pacemaker and the heart, for example by passing the electrode along a vein to an interior region of the heart at which sensing and pacing will occur. Typical pacemaking leads are constructed with one or more coils of conducting wire which are covered by an outer sheath of an insulating material, for example polyurethane, to form the body of the lead. The lead has a proximal end with a connector which is plugged into the pacemaker and a distal electrode end which is affixed to heart tissue to stimulate the tissue and detect electrical cardiac signals.

The distal end of typical pacemaking leads includes an electrically conducting tip which is held against the cardiac tissue. If the lead is unipolar, this tip electrode defines the active part of a circuit between the heart and the pacemaker and the electrically conducting housing of the pacemaker provides the ground for this circuit. The unipolar lead thus has a single coil of wire which connects the pacemaker at one end to the pacing and sensing tip electrode at the other.

A bipolar pacing lead has the above-described tip electrode disposed at its distal end and an associated ring electrode disposed on the body of the lead, usually approximately 2 centimeters from the tip. The bipolar lead body typically includes two coaxially disposed conducting coils which are insulated from one another. One of the coils is conductively connected to the tip electrode and the other of the coils is conductively connected to the ring electrode. Pacing and sensing of cardiac tissue is thus achieved between the active tip electrode and passive ring electrode.

Bipolar pacing leads with the above-described structure have been found adequate for sensing electrical activity of the ventricle and pacing the ventricle. In operation, the pacing lead is disposed so that the tip electrode contacts the wall of the heart in the ventricle and senses electrical activity in a field defined between the tip and ring electrodes. This electrode structure has been found adequate to detect electrical QRS signals (R-waves) which cause natural contraction of the ventricle. If the tip electrode of the pacing lead is placed against the right ventricle, such QRS signals have a sufficiently large amplitude to be relatively easily detected by circuitry in the remote implanted pacemaker. Although natural electrical activity occurs synchronously in the atrium and ventricle, it has been found that the natural atrial signal or P-wave is so low in energy that it does not interfere with the detection of the relatively powerful QRS signal in the ventricle. Thus, when sensing in the ventricle, the amplifiers of the signal detection circuitry of the pacemaker may relatively easily detect QRS signals.

However, when the pacing lead is disposed in the atrium in order to detect atrial P-waves, it has been found that the high energy QRS signal is also detected and thus interferes with the detection of the atrial signal. Relatively complex circuitry has been utilized in the art in an effort to distinguish P-waves and QRS signals in the atrium, so that the pacemaker will respond only to the detection of P-waves. Such circuitry adds to the expense and complexity of the pacemaker and increases the battery power requirements, thus reducing the useful life of the pacemaker within the body. The added complexity of such circuitry is also undesirable in that it reduces the reliability of the pacing system. Moreover, in discriminating between R-waves and P-waves, there is always the chance that an error will be made and the patient's heart will be unnecessarily stimulated.

Accordingly, it is an object of the invention to provide a pacing lead with a structure that will allow P-wave signals to be detected in the atrium with enhanced sensitivity and that will discriminate such atrial signals from R-waves of the ventricle.

Another object of the invention is to provide such a pacing lead with a tip portion which supports two closely spaced electrodes that contact cardiac tissue, for example tissue in the atrium, and detect P-wave signals in the near field but do not detect QRS signals in the far field of the lead.

A further object of the invention is to provide such a bipolar pacing lead which includes a tip electrode at its distal end for stimulating the atrium and an associated coaxially disposed inner electrode in insulated relation with the tip electrode for sensing electrical signals in conjunction with the tip electrode.

Another object of the invention is to provide such an electrode with bifilar coils independently insulated and disposed in intermeshing relationship within the body of the pacing lead and respectively conductively connected to the two electrodes at the distal end of the lead.

A further object of the invention is to provide a pacing lead with enhanced sensitivity which includes a tip electrode disposed in insulated relation to an associated affixation element having electrically conducting tines, the tines and the tip electrode being electrically connected to the pacer to provide the pacing and sensing functions.

These and other objects of the invention will be understood by reference to the drawings and to the detailed description of preferred embodiments, wherein like elements are identified by the same reference numerals.

SUMMARY OF THE INVENTION

The body implantable pacing lead of the invention includes a distal end portion which is disposed to contact cardiac tissue, for example tissue in the atrium of the heart. In one embodiment of the invention an electrically conducting tip electrode is disposed at the distal end of the lead and an associated inner electrode is disposed in insulated coaxial relation with the tip electrode to sense atrial P-waves with the tip electrode. The distal end of the lead further includes an insulated corkscrew which affixes the electrodes in conductive contact with the cardiac tissue.

A second embodiment of the lead of the invention has a distal portion which includes split-tip electrodes that are disposed in closely spaced, insulated relation with one another to detect electrical signals of adjacent abutting cardiac tissue.

A third embodiment of the lead of the invention has an electrically conducting tip electrode disposed at its distal end for stimulating cardiac tissue and two sense electrodes embedded in insulated relation within and extending from the face of the tip electrode to contact cardiac tissue for sensing electrical signals.

A fourth embodiment of the lead of the invention has a tip electrode disposed at its distal end for pacing cardiac tissue and an associated electrically conducting tine assembly disposed in insulated relation to the tip electrode for affixing the electrode to cardiac tissue and operating with the electrode to detect cardiac signals.

A fifth embodiment of the invention has an electrically conducting tip electrode disposed at its distal end and an associated inner electrode coaxially disposed in insulated relation with the tip electrode. The electrodes are conductively connected with the pacemaker by a lead body which includes conducting bifilar coils that are independently insulated and intermeshed to provide a lower profile for the lead body.

BRIEF DESCRIPTION OF THE DRAWINGS

FIG. 1 illustrates a perspective view of a heart pacemaker and an interconnected heart pacemaker lead of an embodiment of the invention.

FIG. 2 illustrates a perspective, partially cross-sectional view of the distal portion of the lead of FIG. 1.

FIG. 3 illustrates a cross-sectional view taken along a line 3—3 of the pacemaker lead of FIG. 2.

FIG. 4 illustrates a partial cross-sectional view of the distal end of the pacer lead of FIG. 2, taken along a line 4—4.

FIG. 5 illustrates an end elevation of the distal end portion of the pacing lead of FIG. 4, as viewed in the direction of the arrows 5—5.

DETAILED DESCRIPTION OF PREFERRED EMBODIMENTS

Figure 6:
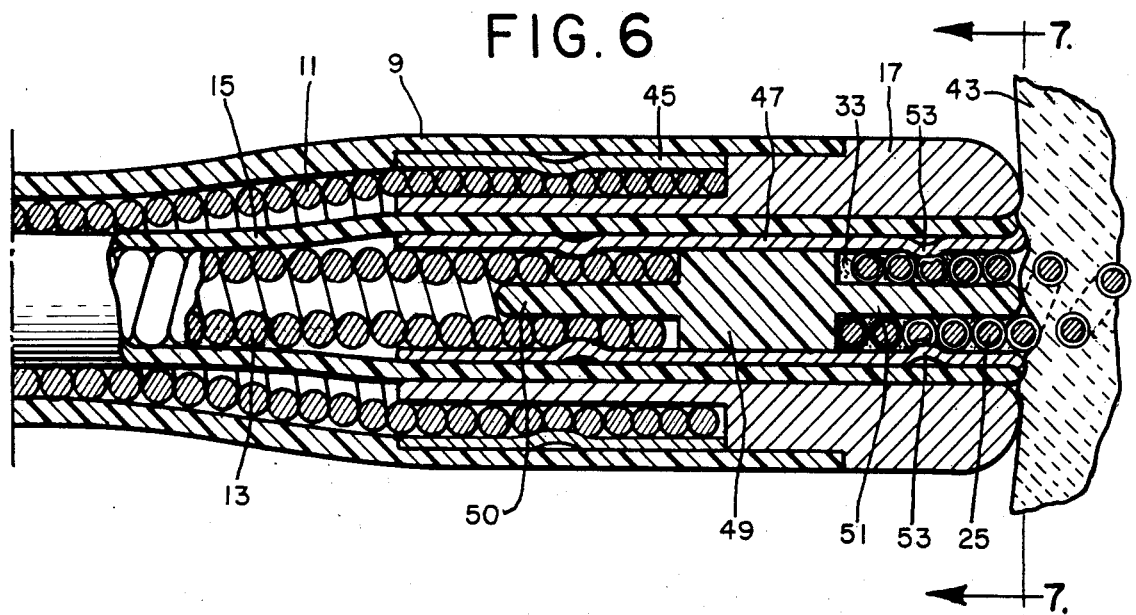
FIG. 6 illustrates a cross-sectional view of the distal end portion of an alternative embodiment of the pacing lead of the invention.

FIG. 1 illustrates a perspective view of a heart pacemaker 1 and an associated lead 3 which includes a proximal connector portion 5 that plugs into a mating connector of the pacemaker and a distal head portion 7 that may be passed along a vein to lodge within the interior of the heart. The lead 3 contains electrically conducting wires which connect the proximal connector 5 and distal head portion 7 so that electrical signals can be transmitted from the pacemaker to stimulate the heart at the tip of the distal head portion 7. The conductors also allow electrical signals occuring in the heart to be transmitted from the distal head portion to the pacemaker for detection by circuitry within the pacemaker. It is generally understood in the art that the heart pacemaker 1 may include circuitry for sensing electrical activity of the heart and generating pacing signals as required by the heart.

FIG. 2 illustrates a perspective view in partial section of the distal head portion 7 of the lead 3. As shown in FIG. 2, the lead includes an outer sheath 9 which may be made of any suitable biocompatible insulating material, for example polyurethane or silicone rubber. The lead includes an outer electrically conducting coil of wire 11 and an associated coaxially disposed inner electrically conducting coil 13 which are separated by an insulating sheath 15 which may be made of any suitable, biocompatible insulating material such as polyurethane or silicone rubber.

FIG. 3 illustrates a cross-sectional view of the distal head portion 7 of the lead 3 taken along a line 3—3. FIG. 3 illustrates the outer flexible insulating sheath 9, conducting coils 11 and 13 and inner insulating sheath 15.

FIG. 4 illustrates a cross-sectional view of the distal head portion 7 of FIG. 2 taken along line 4—4. As shown in FIG. 4, the distal end of the lead includes a first electrically conducting tip electrode 17 and second electrically conducting inner electrode 19 with a wire portion 23 and a conducting ball tip 21. The electrode 17 may be made of any suitable biocompatible metal, such as a platinum-iridium alloy, titanium, carbon, or a carbon coated porous sintered titanium. The wire 23 of the inner electrode may be made of a conducting nickel-cobalt alloy such as is known in the art and the ball tip may be made of platinum, carbon, or any other known biocompatible conducting material.

The tip electrode 17 has a chamber 16 formed therein which contains a corkscrew affixation element or anchor 25 which is made of a coil of conducting wire with a coating of insulating material 29, for example Parylene C manufactured by Union Carbide. The wire of the anchor 25 may be made of a nickel-cobalt alloy or stainless steel. The distal portion of the wire 23 of the inner electrode 19 is supported within the anchor 25 by a sleeve 31 which may be made of any suitably rigid material, for example titanium or stainless steel. The assembly which includes the anchor 25, sleeve 31 and distal portion of the wire 23 is disposed within the chamber 16 of the tip electrode 17. The anchor 25, sleeve 31 and distal portion of the wire 23 are potted within the chamber 16 by a suitable medical adhesive 33, for example a silicone rubber adhesive such as Medical Adhesive Type A made by Dow Corning.

As previously described, the lead includes an outer conducting coil 11 and an associated coaxially disposed inner conductive coil 13 which run along the lead 3 and conductively connect the tip electrode 17 and inner electrode 19 with the proximal connector 5 of the lead. The wire 23 of the inner electrode 19 is conductively connected with the outer coil 11 by an electrically conducting crimp connector 35 made of, for example titanium or stainless steel. The crimp connector 35 is a sleeve into which the ends of the wires 11 and 23 are inserted. A tool is employed to crimp the connector 35 and thus hold the ends of the wires in conductive connection.

The inner coil 13 of the lead is disposed within a chamber 37 which is formed by the electrically conducting body of the tip electrode 17. The inner coil 13 is held in conductive connection with the body of the tip electrode 17 by the interaction of crimp portions 39 and an inner stake 41 which may be made of a suitably rigid material, for example titanium or stainless steel. In operation, the stake 41 is initially inserted into the end of the inner coil 13 and the coil is then inserted within the chamber 37 of the tip electrode 17. Thereafter, the body of the tip electrode 17 is crimped at the crimp portions 39 to compress the inner coil 13 against the stake 41 and thus hold the inner coil in firm conductive contact with the body of the tip electrode 17.

It should be understood that the outer and inner coils 11 and 13 are separated in insulated relation by the inner insulating sleeve 15 which also extends along the body of the tip electrode 17 to insulate the crimp connector 35 and wire 23 from the electrode 17. It should be further understood that the medical adhesive 33 within the chamber 16 holds the distal portion of the wire 23 in insulated relation with respect to the tip 17. Thus, the coils 11 and 13 respectively conductively connect the tip electrode 17 and its associated coaxial inner electrode 19 with the pacemaker 1.

A polyurethane adhesive is used to glue and seal the outer polyurethane sheath 9 and inner polyurethane sheath 15 to the shank of the electrode 17. If the sheaths are made of silicone rubber, a suitable silicone rubber adhesive such as Medical Adhesive Type A should be used.

It should further be understood that the corkscrew anchor 25 is held within the chamber 16 of the tip electrode 17 by the interaction of crimp portions 32 with the rigid sleeve 31. In operation, the wire 23 is passed through the sleeve 31 and the sleeve and wire are then inserted within the chamber 16. Thereafter, the corkscrew anchor 25 is disposed around the sleeve 31 in coaxial relationship with the sleeve and the medical adhesive 33 is injected into the chamber 16 and is allowed to solidify to pot the elements within the chamber. The body of the tip electrode 17 is crimped at the crimp portions 32 to hold the corkscrew anchor within the chamber 16 with approximately three turns of the corkscrew anchor extending outside the front face of the electrode 17.

In operation, the lead assembly of FIGS. 1-5 is positioned in the atrium in a manner known to the art, so that the anchor abuts the wall of the atrium. Thereafter, the flexible lead 3 is twisted so that the projecting end of the insulated corkscrew anchor 25 turns into the cardiac tissue 43 of the atrium. The lead is turned until the end of the corkscrew anchor 25 is fully embedded within the atrium with the front face of the tip electrode 17 and the ball tip 21 of the inner electrode 19 held in conductive contact against the tissue 43.

When the distal end of the pacing lead of FIGS. 1-5 is thus affixed within the atrium, the tip electrode 17 and associated inner electrode 19 may be utilized as bipolar electrical elements to stimulate the cardiac tissue 43. Alternatively, the tip electrode 17 may be utilized as an active electrode with respect to the conducting body of the pacer 1 to stimulate the cardiac tissue 43 in the manner of a unipolar lead.

When it is desired to detect electrical P-waves in the atrium, the tip electrode 17 and inner electrode 19 are employed as bipolar electrode sensing elements. The electrode structure of FIG. 4 has been experimentally tested in canines to determine its sensitivity to atrial P-waves. The sensitivity is defined as the ratio of the magnitude in volts of the detected P-wave and the magnitude in volts of the associated detected R-wave in the atrium. In experimental use, the electrode assembly of FIGS. 1-5 detected canine P and R-waves between the tip electrode 17 and inner electrode 19 with a P/R ratio of 15.83. This P-R ratio was compared with a P/R ratio of 1.21 which was measured by sensing between the tip 17 of the electrode and a remote ground plate which was employed to simulate unipolar sensing with respect to the conducting body of a pacer. A P/R ratio of 2.29 was detected for sensing between the inner electrode 19 and the remote ground plate.

It should be understood that a relatively high P/R ratio is desirable because it provides a sensed atrial P-wave at the pacer 1 which is much greater in amplitude than an associated background R-wave from the ventricle. Thus, the lead of the invention substantially increases the signal to noise ratio of the detected atrial signal. The circuitry of the pacemaker 1 therefore relatively easily detect P-waves in the atrium and ignore or disregard the corresponding relatively low amplitude R-waves. This substantially enhanced sensitivity for atrial signals is advantageous, because it allows easy detection of atrial P-waves without requiring relatively sophisticated and complex circuitry for discriminating between P-waves and R-waves. The structure of the lead of FIGS. 1-5 thus enhances the sensitivity of the pacemaker to signals in the atrium.

It is theorized that the enhanced sensitivity of the electrode structure of FIGS. 1-5 is achieved because the combination of the electrodes 17 and 19 results in shorting out the far field electrical activity of the ventricle. The electrodes thus detect a strong signal only in the immediate vicinity of the tissue which is contacted. The electrodes 17 and 19 are therefore sensitive to P-waves which occur in the atrium and which pass directly over the electrodes and are much less sensitive to far field R-waves which occur in the ventricle. It is theorized that typical pacing leads do not achieve this result, at least because the ring electrode in such leads is held away from the cardiac tissue which is contacted by the tip electrode.

In the structure of the electrode of FIGS. 1-5, the tip electrode 17 is about 2 mm in diameter and is therefore less than 1 mm from the inner electrode 19. It is believed that the direct contact of these closely spaced electrodes with the cardiac tissue provides the enhanced sensitivity of the lead to near field atrial signals. A lead having this or a corresponding structure within the scope of the invention could be utilized in other areas of the body to achieve an enhanced sensitivity to local electrical signals and a reduced sensitivity to far field electrical signals from other areas of the body or external to the body.

The electrode assembly of FIG. 4 utilizes the helical anchor 25 to firmly hold the electrodes 17 and 19 in conductive contact with cardiac tissue. The helical anchor ensures that the electrode 19 will not become dislodged from the tissue and thus reduce the sensitivity of the lead to atrial signals. It should be understood that the helical anchor 25 is insulated from the electrodes 17 and 19 so that the tissue traumatized by entry of the anchor is not paced or sensed.

FIG. 5 illustrates an end elevation of the distal head portion of the pacing lead of FIG. 4, as viewed in the direction of the arrows 5—5. FIG. 5 is provided to illustrate the coaxial relationship of the head of the electrode 17, ball 21 of the inner electrode 19 and insulated coils of the anchor 25.

FIG. 6 is a cross-sectional view of the distal end portion of an alternative embodiment of the pacing lead of the invention. As shown in FIG. 6, the tip electrode 17 is conductively connected to its associated outer coil 11 by a conducting sleeve 45 which may be made of a relatively rigid material, for example titanium or stainless steel. The sleeve 45 is crimped inwardly so that it presses the coil 11 in firm conductive connection with a shank portion of the tip electrode 17.

An inner conducting electrode sleeve 47 is disposed within the tip electrode 17 in coaxial relation with the electrode. The electrode sleeve 47 may be made of any suitable electrically conducting and biocompatible material, for example platinum, titanium or a platinum-iridium alloy such as is known in the art. The sleeve 47 is held in insulated relation with respect to the tip electrode 17 by the insulating sleeve 15 which separates the coils 11 and 13.

The inner coil 13 is conductively connected to the inner electrode sleeve 47 by a crimping interaction between the sleeve 47 and an associated stake 49 which may be made of a relatively rigid material, for example titanium or stainless steel. In operation, a post 50 of the stake 49 is disposed within the inner coil 13 and the electrode sleeve 47 is crimped to provide a firm conductive connection between the coil 13 and the sleeve.

The insulated corkscrew anchor 25 is disposed within an annular chamber defined between the wall of the electrode sleeve 47 and a post 51 of the stake 49. The anchor 25 is affixed within the end of the sleeve 47 by crimping at crimp points 53 against the post 51.

Figure 7:
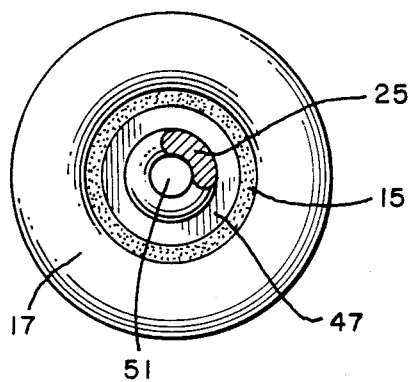
FIG. 7 illustrates an end elevation of the pacing lead of FIG. 6 in partial section, taken along a line 7—7.

FIG. 7 illustrates an end elevation of the distal electrode assembly of FIG. 6 as seen in the direction of the arrows 7—7. The insulated corkscrew anchor 25 is potted within the electrode sleeve 47 by a medical adhesive such as Medical Adhesive Type A. It should generally be understood that a polyurethane adhesive is used to affix and seal the tip electrode 17 to the polyurethane insulating sleeve 15 and the sleeve 15 to the inner electrode sleeve 47. This adhesive is also used to glue and seal the outer insulating sheath 9 to the outer surface of the conducting sleeve 45 and a portion of the outer surface of the tip electrode 17. If the insulating sheaths are made of silicone rubber, another adhesive such as Medical Adhesive Type A is used.

In operation, the pacing lead of FIG. 6 operates in the same manner as the lead described with respect to FIGS. 1-5. Thus, the protruding end peripheral surface of the sleeve 47 is the inner electrode and the tip electrode 17 is the outer electrode of the bipolar lead. As previously discussed, an enhanced sensitivity to atrial P-waves results when these closely spaced electrodes are held in contact with atrial cardiac tissue 43 by the insulated corkscrew anchor 25.

Figure 8:
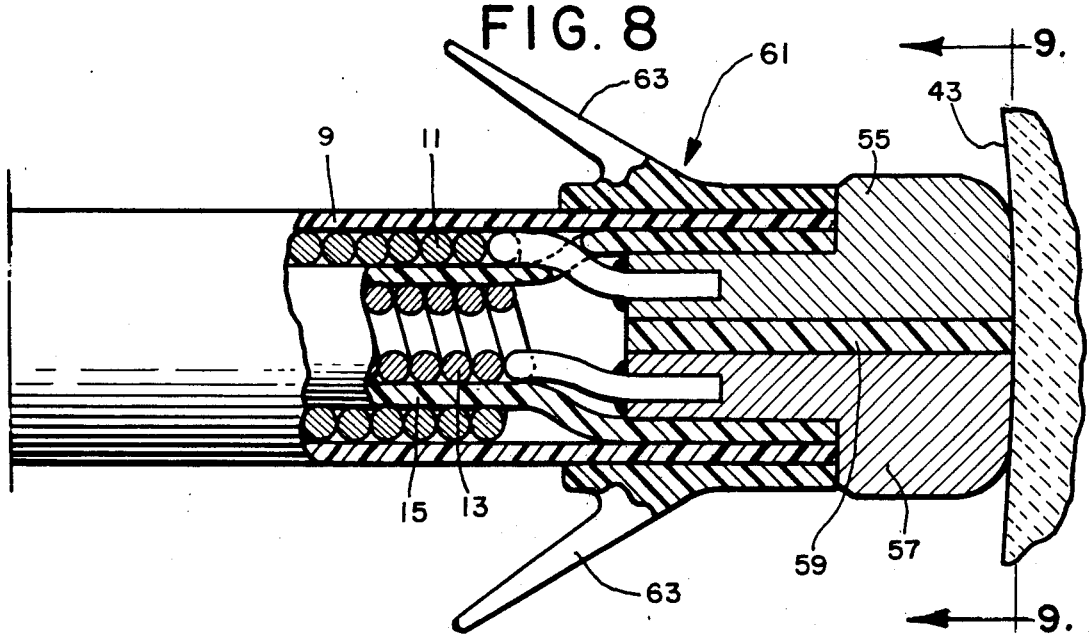
FIG. 8 illustrates a cross-sectional view of the distal end portion of another alternative embodiment of the pacing lead of the invention.

FIG. 8 illustrates the distal end portion of another embodiment of the pacing lead of the invention. As illustrated in FIG. 8, the pacing lead has split electrically conducting electrodes 55 and 57 which may be made of any known biocompatible electrode material, such as a platinum-iridium alloy or titanium. Alternatively, the electrodes 55 and 57 may be constructed with a solid titanium shank and an associated carbon coated porous tip made from sintered grains of titanium.

Figure 9:
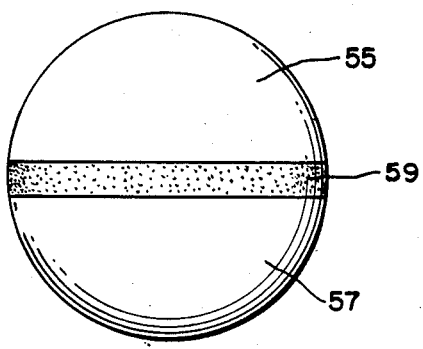
FIG. 9 illustrates an end elevation of the pacing lead of FIG. 8, viewed in the direction of the arrows 9—9.

The end elevation view of FIG. 9 illustrates the front end portions of the split electrodes 55 and 57 as seen in the direction of the arrows 9—9 of FIG. 8. It can be seen with reference to FIGS. 8 and 9 that the split electrodes 55 and 57 are supported in insulated relation by an insulating pad 59 which may be made, for example of silicone rubber or polyurethane and which is affixed in sealed relation to the electrodes 55 and 57 by any known medical adhesive such as is previously discussed.

The ends of the electrically conducting coils 11 and 13 are inserted into holes drilled in the shanks of the split electrodes 55 and 57, respectively. The wires 11 and 13 are held in conductive connection with the split electrodes 55 and 57 by a medical adhesive or possibly by a biocompatible solder material.

As illustrated in FIG. 8, the distal end of the lead has a tine assembly 61 which may be made of a relatively flexible, biocompatible material such as silicone rubber. The assembly 61 is glued to the outer sheath 9 of the lead by any suitable known biocompatible medical adhesive. In operation, tines 63 hold the electrodes 55 and 57 against cardiac tissue 43 by intermeshing with adjacent tissue of the heart. The electrode of FIG. 8 senses atrial signals of the tissue 43 between the closely spaced split electrodes 55 and 57.

Figure 10:
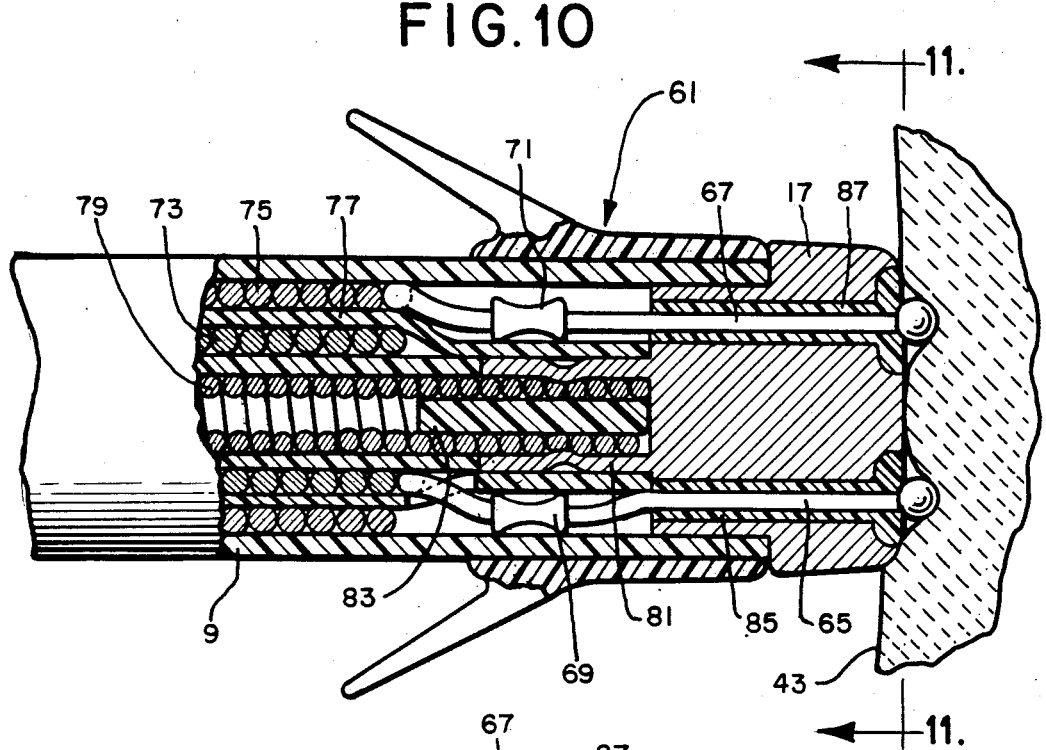
FIG. 10 illustrates a cross-sectional view of the distal end portion of another alternative embodiment of the pacing lead of the invention.

FIG. 10 illustrates a cross-sectional view of the distal end portion of another embodiment of the pacing lead of the invention. The lead of FIG. 10 has three electrodes at its distal end. The first of these electrodes 17 is employed to pace the cardiac tissue 43 with respect to a ground provided by either the conducting housing of the pacer 1 or either or both of associated sensing electrodes 65 and 67.

The sensing electrodes 65 and 67 are respectively conductively connected by crimp sleeves 69 and 71 to associated electrically conducting coils 73 and 75. The coils 73 and 75 are separated by an insulating sleeve 77 which may be made of polyurethane or silicone rubber.

The tip electrode 17 is conductively connected to an inner coil 79 by crimping a sleeve portion 81 of the electrode 17 against the coil 79 and an associated stake 83 which may be made of a relatively rigid material, such as titanium or stainless steel. The lead of FIG. 10 also includes a tine assembly 61 which is affixed to the outer sheath 9 of the lead body by medical adhesive.

The sensing electrodes 65 and 67 are constructed in the manner generally described for the electrode 19 of FIG. 4. Each of the electrodes 65 and 67 are held in insulated relation with respect to the tip electrode 17 by insulating sleeves 85 and 87 which may be made of, for example silicone rubber. Alternatively, the electrodes may be potted within the electrode 17 by a suitable insulating medical adhesive such as Medical Adhesive Type A.

Figure 11:
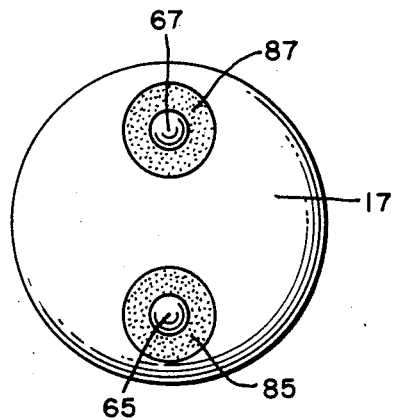
FIG. 11 illustrates an end elevation of the pacing lead of FIG. 10, viewed in the direction of the arrows 11—11.

FIG. 11 shows an end elevation of the tip of the electrode of FIG. 10 as viewed in the direction of the arrows 11—11. As shown in FIGS. 10 and 11, the electrodes 67 and 65 and the tip electrode 17 abut cardiac tissue 43 to stimulate and sense the tissue. In operation, the electrode 17 is employed to stimulate the cardiac tissue 43 and the electrodes 65 and 67 are employed to detect electrical signals of the tissue.

The three-wire system of the lead of FIG. 10 is thus used to stimulate the heart with the large electrode 17 and to sense atrial signals with enhanced sensitivity between the electrodes 67 and 65.

Figure 12:
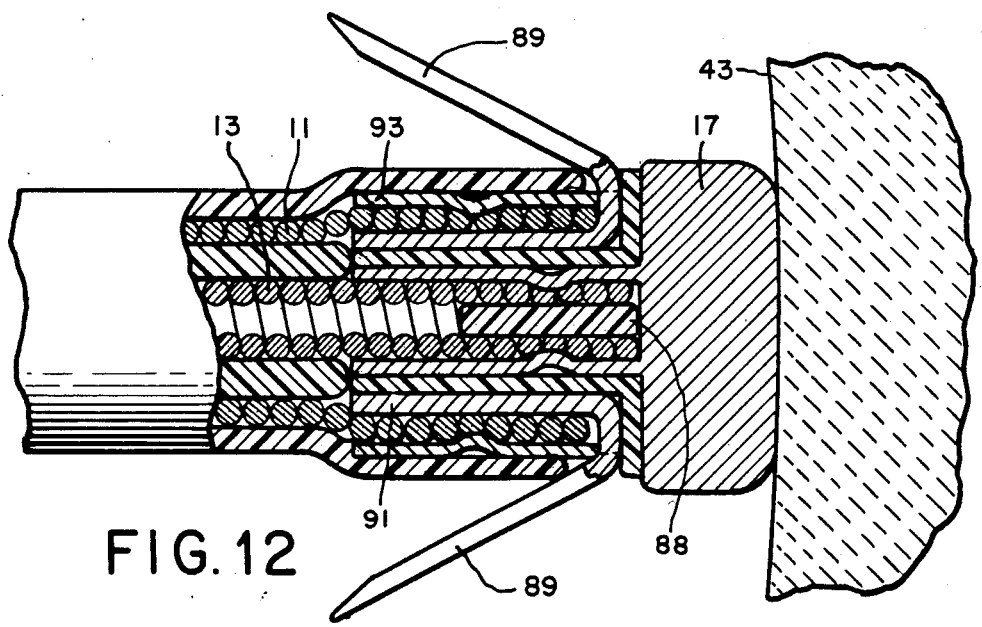
FIG. 12 illustrates a cross-sectional view of the distal end portion of another alternative embodiment of the pacing lead of the invention.

FIG. 12 illustrates an alternative embodiment of the pacing lead of the invention which employs an electrically conducting tine assembly 89 as an electrode of the pacing lead. The tine assembly 89 is mounted in insulated relation with the tip electrode 17 by an insulating sleeve 91 which may be made of, for example polyurethane or silicone rubber. The tip electrode 17 is crimped to the inner conducting coil 13 against a titanium or stainless steel stake 88 in the manner previously described. The conducting tine assembly 89 is conductively connected to the outer coil 11 by an electrically conductive crimped sleeve 93, made of for example titanium or stainless steel. The tine assembly 89 may be made of a biocompatible metal, for example titanium or a conducting elastomer, for example silicone rubber impregnated with carbon. It is theorized that the projecting tines of the conducting tine assembly 89 will engage cardiac tissue adjacent to the tissue contacted by the electrode 17 and will therefore be sufficiently close to the electrode 17 to provide enhanced detection of atrial cardiac signals.

Figure 13:
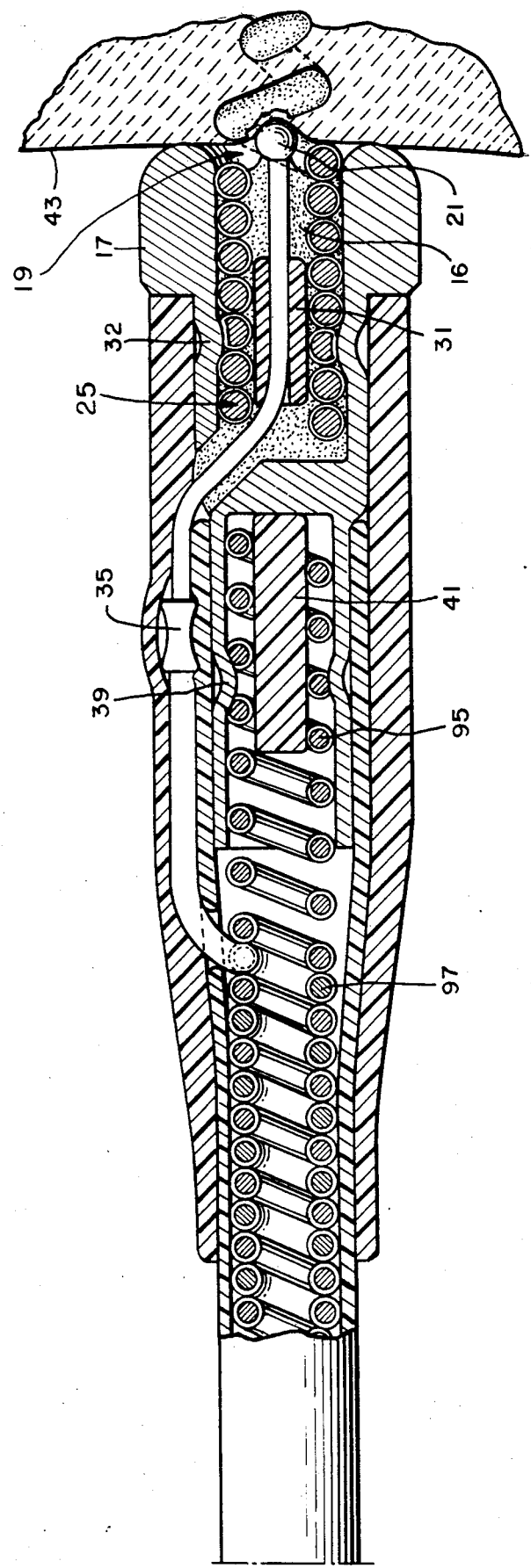
FIG. 13 illustrates a cross-sectional view of a distal end portion of another alternative embodiment of the pacing lead of the invention.

FIG. 13 illustrates a cross-sectional view of the distal end portion of another alternative embodiment of the lead of the invention. As shown in FIG. 13, intermeshed conductive coils 95 and 97 are used for the body of the lead. The coils are independently insulated so that they do not short against one another within the lead. Thus, a first coil 95 made of, for example, a nickel-cobalt alloy is intermeshed with a second metal coil 97 of the same material. Each of the coils is covered with an insulating layer which is preferably an extruded coating of polyurethane. The coil 95 is conductively connected to the shank of the tip electrode 17 by crimping the coil against a stake 4 made of titanium or stainless steel. In operation, the crimps 39 cut through the insulation of the coil to provide a good electrical connection between the coil and the electrode 17. The coil 97 is conductively connected to the inner electrode 19 of the lead by removing the insulation from the end of the coil and crimping this end to the end of the inner electrode in the manner described for the embodiment of FIGS. 1-5. The advantage of the electrode of FIG. 13 is that the intermeshed bifilar coils provide a flexible lead body which has a relatively small diameter.

Although the disclosed embodiments of the lead of the invention have two sensing electrodes, it should be understood that any desired number of sensing electrodes may be used, so long as at least two of the electrodes contact tissue, for example atrial tissue, to detect near field signals. Also, although the disclosed embodiments have sensing electrodes disposed on the distal tip of a single lead body, it should be appreciated that sensing electrodes may be placed on different lead bodies or on different portions of a single lead body, so long as at least two sensing electrodes simultaneously contact tissue in a desired area to detect near field signals.

Although particular embodiments of the lead assembly of the invention have been disclosed, it should be understood that these embodiments are provided only for illustrative purposes and are not intended to limit the scope of the invention. Accordingly, the invention may be embodied in other specific forms without departing from its spirit or essential characteristics. The present embodiments are, therefore, to be considered in all respects as illustrative and not restrictive, the scope of the invention being indicated by the claims rather than by the foregoing description. Accordingly, all changes which come within the meaning and range of the equivalents of the claims are intended to be embraced therein.

We claim:

1. In a pacemaker lead of a type having a proximal end for conductively connecting with a cardiac pacemaker, a distal end with electrodes for conductively contacting cardiac tissue and conducting wires for conductively connecting the electrodes of the distal end with the proximal end, the improvement comprising:
   at least two bipolar electrodes disposed at said distal end for simultaneously conductively contacting a selected area of cardiac tissue and transmitting to said pacemaker over said wires cardiac signals detected between the electrodes; and
   means supporting said at least two bipolar electrodes in insulated relation with respect to one another for maximizing the detected amplitude of cardiac signals occurring in the area adjacent the electrodes with respect to the detected amplitude of cardiac signals occurring at a greater distance from said electrodes.

2. The pacemaker lead of claim 1, wherein said selected area of cardiac tissue is an area of the atrium of a heart and said means for supporting including means for defining an electrode spacing at which the ratio of the detected amplitude of atrial signals with respect to the detected amplitude of ventricular signals is maximized to facilitate detecting said atrial signals.

3. The pacemaker lead of claim 1, wherein one of said electrodes includes a conducting electrode wire with a conducting ball at a free end thereof and the other of said electrodes is a conducting electrode sleeve, said means for supporting including insulating means for holding said electrode wire in insulated coaxial relation within said electrode sleeve, so that the ball and sleeve extend to simultaneously conductively contact said selected area of cardiac tissue.

4. The pacemaker lead of claim 1, further including a helical anchor for holding said electrodes in conductive contact with said cardiac tissue.

5. The pacemaker lead of claim 4, including means for insulating said helical anchor with respect to said electrodes.

6. The pacemaker lead of claim 1, wherein said means for supporting includes means for supporting said electrodes at a selected spacing of no more than one millimeter.

7. The pacemaker lead of claim 1, wherein one of said electrodes is an outer conducting sleeve having a front contact surface in a contact plane and the other of said electrodes is an inner conducting sleeve located within said outer sleeve and having a front contact surface in said plane and disposed radially inwardly of the front contact surface of the outer sleeve.

8. The pacemaker lead of claim 1, wherein one of said electrodes forms a conducting plate defining a first contact surface in a contact plane and the other of said electrodes forms another conducting plate defining a second contact surface in said plane.

9. The pacemaker lead of claim 1, wherein each of said electrodes includes a conducting electrode wire with a conducting ball at a free end thereof.

10. The pacemaker lead of claim 1, wherein one of said electrodes forms a conducting plate disposed in a front contact plane and the other of said electrodes is a conducting affixation means having conducting tines for holding said conducting plate against cardiac tissue and for conductively contacting adjacent cardiac tissue.

11. A pacemaker lead for providng a conductive connection between atrial cardiac tissue and a pacemaker and enhancing the detection of near field atrial electrical signals with respect to far field ventricular electrical signals, comprising:
at least two bipolar electrodes for simultaneously contacting the atrium of a heart;
means for conductively connecting said electrodes with said pacemaker for detecting electrical signals between said electrodes; and
means mounting said electrodes in insulated relation and disposd against said surface of the atrium with an electrode spacing for maintaining at least a selected ratio between the detected amplitude of atrial signals and the detected amplitude of ventricular signals, to facilitate detection of atrial signals.

12. The pacemaker lead of claim 11, wherein one of said electrodes includes a conducting electrode wire with a conducting ball at a free end thereof and the other of said electrodes is a conducting electrode sleeve, said means for mounting including insulating means for holding said electrode wire in insulated coaxial relation within said electrode sleeve, so that the ball and sleeve extend to simultaneously conductively contact the atrium.

13. The pacemaker lead of claim 1, further including a helical anchor for holding said electrodes in conductive contact with the atrium.

14. The pacemaker lead of claim 13, including means for insulating said helical anchor with respect to said electrodes.

15. The pacemaker lead of claim 11, wherein said means for mounting includes means for supporting said electrodes at an electrode spacing of no more than one millimeter.

16. The pacemaker lead of claim 11, wherein one of said electrodes is an outer conducting sleeve having a front contact surface in a contact plane and the other of said electrodes is an inner conducting sleeve located within said outer sleeve and having a front contact surface in said plane and disposed radially inwardly of the front contact surface of the outer sleeve.

17. The pacemaker lead of claim 11, wherein one of said electrodes forms a conducting plate defining a first contact surface in a contact plane and the other of said electrodes forms another conducting plate defining a second contact surface in said plane.

18. The pacemaker lead of claim 11, wherein each of said electrodes includes a conducting electrode wire with a conducting ball at a free end thereof.

19. The pacemaker lead of claim 11, wherein one of said electrodes forms a conducting plate disposed in a front contact plane and the other of said electrodes is a conducting affixation means having conducting tines for holding said conducting plate against the atrium and for conductively contacting the atrium.

20. The pacemaker lead of claim 11, wherein said means for conductively connecting includes at least two insulated intermeshing conducting coils.

21. A lead for conductively connecting body tissue with a device for sensing electrical signals of said tissue, comprising:
at least two bipolar electrodes having contact surfaces for conductively contacting a selected surface of said tissue;
means for conductively connecting said electrodes with said device for detecting electrical signals between said electrodes; and
means mounting said at least two bipolar electrodes in spaced insulated relation at a selected distance from one another with said conduct surfaces lying in substantially the same plane for conductively contacting said surface of said tissue in said plane for maintaining at least a predetermined ratio between the detected amplitude of near field electrical signals generated in the immediate area of said electrodes and the detected amplitude of far field signals generated outside said immediate area of the electrodes for facilitating the detection of said near field signals.

22. The lead of claim 21, wherein said device is a cardiac pacemaker and said means for mounting includes means for holding the contact surfaces of said electrodes against a surface of the atrium of a heart and defining a ratio of the detected amplitude of atrial signals with respect to ventricular cardiac signals to facilitate detection of said atrial signals.

23. The lead of claim 21, wherein one of said electrodes includes a conducting electrode wire with a conducting ball at a free end thereof and the other of said electrodes is a contacting electrode sleeve, said means for mounting including insulating means for holding said electrode wire in insulated coaxial relation with respect to said electrode sleeve, so that the ball and sleeve extend to simultaneously conductively contact said surface of said tissue.

24. The lead of claim 21, further including a helical anchor for holding said electrodes in conductive contact with said surface of said tissue.

25. The lead of claim 24, including means for insulating said helical anchor with respect to said electrodes.

26. The lead of claim 21, wherein said means for mounting includes means for mounting said electrodes at a selected distance of no more than one millimeter.

27. The lead of claim 21, wherein one of said electrodes is an outer conducting sleeve having a front contact surface in said plane and the other of said electrodes is an inner conducting sleeve located within said outer sleeve and having a front contact surface in said plane and disposed said selected distance radially inwardly of the front contact surface of the outer sleeve.

28. The lead of claim 21, wherein one of said electrodes forms a conducting plate defining a first contact surface in said plane and the other of said electrodes forms another conducting plate defining a second contact surface in said plane.

29. The lead of claim 21, wherein each of said electrodes includes a conducting electrode wire with a conducting ball at a free end thereof disposed in said plane.

30. The lead of claim 21, wherein said means for conductively connecting includes at least two insulated intermeshing conducting coils.

31. A pacemaker lead for conductively connecting cardiac tissue with a pacemaker, comprising:
   a lead body including at least two electrically conducting coils of wire and means for conductively connecting proximal ends of said coils of wire to said pacemaker, said lead body further including a first insulating means for insulating said coils of wire from each other and a second insulating means for insulatingly covering the coils of wire;
   a tip electrode means having one polarity and including a conducting contactor and means for conductively connecting said contactor to a distal end of one of said coils of wire;
   a ring electrode means having a polarity opposite said one polarity and including a conductive sleeve having a contact face and means for conductively connecting said sleeve to a distal end of the other of said coils of wire;
   means supporting the tip electrode means in coaxial insulated relation within said conductive sleeve with said contactor disposed adjacent said contact face of the sleeve and spaced a predetermined lateral distance from said contact face for maintaining at least a selected ratio between the detected amplitude of near field electrical signals occurring in the immediate area of the electrodes and the detected amplitude of far field electrical signals occurring outside said immediate area to facilitate the detection of said near field signals; and
   means for holding said contact face and contactor in conductive contact with a selected area of cardiac tissue for transmitting to said pacemaker over said coils of wire cardiac signals detected between the tip and ring electrode means.

32. The pacemaker lead of claim 31, wherein said means for supporting includes means for supporting said electrodes at a predetermined lateral distance of no more than one millimeter.

33. The pacemaker lead of claim 31, wherein said means for holding includes means for holding said contact face and contactor against a surface of the atrium of the heart and said means for supporting includes means for maximizing the amplitude of detected atrial signals with respect to the amplitude of detected ventricular signals to facilitate detecting said atrial signals.

34. The pacemaker lead of claim 31, wherein said means for supporting includes means for supporting said contact face and contactor at a lateral distance of no more than one millimeter.

35. The pacemaker lead of claim 31, wherein said first insulating means is an insulating sheath disposed between said coils of wire.

36. The pacemaker lead of claim 31, wherein said coils of wire are engaged in intermeshing relation and said first insulating means includes an insulating coating for each of said coils of wire.

37. The pacemaker lead of claim 31, wherein said contactor is an electrically conducting ball.

38. The pacemaker lead of claim 31, wherein said means for holding includes a helical anchor for engaging cardiac tissue to hold the electrodes against said tissue and means for insulating said helical anchor from said electrodes.

* * * * *